US009808838B2

(12) United States Patent
Gaus

(10) Patent No.: US 9,808,838 B2
(45) Date of Patent: Nov. 7, 2017

(54) CLEANING DEVICE FOR CONTAINERS FOR HUMAN WASTE

(71) Applicant: MEIKO Maschinenbau GmbH & Co. KG, Offenburg (DE)

(72) Inventor: Bruno Gaus, Offenburg (DE)

(73) Assignee: MEIKO MASCHINENBAU GMBH & CO. KG, Offenburg (DE)

(*) Notice: Subject to any disclaimer, the term of this patent is extended or adjusted under 35 U.S.C. 154(b) by 7 days.

(21) Appl. No.: 14/787,699

(22) PCT Filed: Apr. 30, 2014

(86) PCT No.: PCT/EP2014/058895
§ 371 (c)(1),
(2) Date: Oct. 28, 2015

(87) PCT Pub. No.: WO2014/177648
PCT Pub. Date: Nov. 6, 2014

(65) Prior Publication Data
US 2016/0067747 A1   Mar. 10, 2016

(30) Foreign Application Priority Data

May 2, 2013   (DE) .................. 10 2013 208 060

(51) Int. Cl.
*A61G 9/02*   (2006.01)
*B08B 3/02*   (2006.01)
(Continued)

(52) U.S. Cl.
CPC .............. *B08B 3/02* (2013.01); *A61G 9/02* (2013.01); *A61L 2/07* (2013.01); *A61L 2/22* (2013.01);
(Continued)

(58) Field of Classification Search
CPC ............... B08B 3/02; A61G 9/02; F04D 1/06
See application file for complete search history.

(56) References Cited

U.S. PATENT DOCUMENTS 5,785,504 A * 7/1998 Cote ..................... B01D 61/10
210/195.2
2007/0104608 A1   5/2007 Gaus et al.

FOREIGN PATENT DOCUMENTS

DE        1 503 853      5/1969
DE        3308230 A1     9/1983
(Continued)

OTHER PUBLICATIONS

International Search Report issued in related International Patent Application No. PCT/EP2014/058895, dated Jul. 30, 2014.
(Continued)

*Primary Examiner* — Michael Kornakov
*Assistant Examiner* — Natasha Campbell
(74) *Attorney, Agent, or Firm* — Foley & Lardner LLP

(57) ABSTRACT

A cleaning device for cleaning items to be cleaned is proposed. The cleaning device includes at least one nozzle system for acting on the items to be cleaned with at least one cleaning fluid. Additionally the cleaning device includes at least one pump for conveying the cleaning fluid to the nozzle system, wherein the nozzle system comprises at least one high pressure nozzle and at least one low pressure nozzle. The high pressure nozzle and the low pressure nozzle are connected fluidically to the pump, wherein at least one fluidic switching element for adjusting an inflow of the cleaning fluid to the low pressure nozzle is connected upstream of the low pressure nozzle.

13 Claims, 2 Drawing Sheets

(51) Int. Cl.
    *A61L 2/24*         (2006.01)
    *F04D 1/06*        (2006.01)
    *A61L 2/07*         (2006.01)
    *A61L 2/22*         (2006.01)

(52) U.S. Cl.
    CPC ................ *A61L 2/24* (2013.01); *F04D 1/06* (2013.01); *A61L 2202/14* (2013.01); *A61L 2202/15* (2013.01); *A61L 2202/17* (2013.01); *A61L 2202/24* (2013.01)

(56) References Cited

FOREIGN PATENT DOCUMENTS

| | | | | |
|---|---|---|---|---|
| DE | 19521536 A1 | 12/1996 | | |
| DE | 19812231 A1 | 9/1999 | | |
| DE | 10348344 B4 | 9/2007 | | |
| EP | 0 341 766 B1 | 12/1991 | | |
| EP | 0 516 563 A1 | 12/1992 | | |
| EP | 2495054 A2 * | 9/2012 | ............ | B08B 3/026 |
| WO | WO 2005/072595 A1 | 8/2005 | | |
| WO | WO 2012/107332 A2 | 8/2012 | | |

OTHER PUBLICATIONS

International Preliminary Report on Patentability, including translation of English claims, issued in related International Patent Application No. PCT/EP2014/058895, dated Mar. 31, 2015.
Translation of International Preliminary Report on Patentability issued in related International Patent Application No. PCT/EP2014/058895, dated Nov. 4, 2015.

* cited by examiner

CLEANING DEVICE FOR CONTAINERS FOR HUMAN WASTE

CROSS-REFERENCE TO RELATED APPLICATIONS

This application is a National Phase of International Patent Application No. PCT/EP2014/058895, filed Apr. 30, 2014, which claims priority from related German Patent Application No. 10 2013 208 060.3, filed May 2, 2013. The contents of these applications are incorporated herein by reference in their entirety.

SCOPE OF THE INVENTION

The invention relates to a cleaning device and to a method for cleaning at least one container for accommodating human waste. These types of cleaning devices and methods are used, for example, in the hospital or care sector in order to clean, and as an option disinfect, containers such as, for example, chamber pots, bed pans, bedpans or other containers, which are suitable for accommodating human or animal waste. These types of cleaning devices are used, for example, as cleaning and disinfecting equipment.

PRIOR ART

A plurality of cleaning devices and cleaning methods for treating containers for accommodating human waste are known from the prior art. The containers to be treated can contain larger volumes of liquid or quantities of solid waste which usually have to be disposed of during the cleaning process. In addition, these types of containers can contain infectious waste or can be contaminated in another manner such that, along with emptying, disinfection is also usually necessary. This type of cleaning equipment for treating containers for human waste is accordingly frequently also designated as washing and disinfecting equipment (WD).

In addition, heavy soiling can occur in the case of such containers such that during the cleaning, in addition to a usual emptying, an increased abrasive power is necessary. In particular, in addition to being acted upon with a cleaning fluid at low pressure, it may be necessary to clean the containers by means of a treatment with a stronger abrasive power, in particular by being acted upon with a cleaning fluid at high pressure.

Along with the named containers, said cleaning devices are basically also suitable for cleaning other medical objects such as are used, for example, in hospitals and geriatric care facilities. The items to be cleaned, however, usually consist of urine bottles, bed pans, kidney dishes, wash bowls or similar containers, the cleaning of which can involve the disposal of larger quantities of waste.

For example, a cleaning device can be developed such as described in DE 10 348 344 B4. DE 103 48 344 B4 discloses a device for carrying out a method for cooling items that have been cleaned and disinfected. The device comprises a chamber which can be acted upon by a water/vapor unit both with cold water or hot water and also with water vapor. The cold water or hot water input is effected by means of spray nozzles. A washing or cleaning program which includes cleaning steps and a disinfection step is executed in the device.

In addition, the prior art, for example DE 10 348 344 B4, makes known cleaning devices which comprise a pump which is set up to convey the cleaning fluid under pressure to at least one nozzle in a cleaning chamber, by means of which items for cleaning located in the cleaning chamber can be acted upon with cleaning fluid. The pump conveys the cleaning fluid for example from a collecting chamber on the floor of the cleaning chamber or from a different storage container to the at least one nozzle.

DE 198 12 231 A1 discloses a dishwasher with a rinsing liquid pump and two spray arms, it being possible to adjust the pressure of the spray arms in a varied manner by means of valves. DE 195 21 21 536 C2 describes a high pressure cleaner with two pumps which are actuatable in a selective manner. DE 33 08 230 A1 also describes high pressure cleaning devices with a high pressure mode and a low pressure mode. DE 1 503 853 describes a dishwasher with a multiple-stage centrifugal pump which is realized for two different speeds.

Where the items to be cleaned are heavily soiled, it can be necessary to increase the pressure at which the cleaning fluid exits from an opening of an impacting device, in particular a nozzle. For example, said increase in pressure could be realized by a high pressure cleaning system provided in the cleaning system. An increase in pressure when using the same nozzles, as in a cleaning device without a high pressure system, could however be disadvantageous as a volume flow of the cleaning fluid used is also increased. By using an impacting device with a smaller opening, the volume flow can basically be reduced. Thus, with a smaller volume flow than for example in the case of low pressure cleaning systems, an identical or even higher energy content of the sprayed cleaning solution and consequently an improved cleaning result can be achieved using high pressure cleaning systems. For example, it could be possible to provide several cleaning systems in the cleaning device, for example a low pressure and a high pressure cleaning system, to improve a cleaning result. Where a low pressure and a high pressure system are incorporated in one cleaning device, however, increased expenditure on hardware, increased installation volume and also increased production costs caused by necessary additional components are to be expected. Thus, for example a plurality of pumps, line systems and impacting devices, in particular nozzles, would have to be installed.

OBJECT OF THE INVENTION

It is consequently the object of the present invention to provide a cleaning device and a method for cleaning a container for human waste which avoid the disadvantages of known devices and methods at least extensively. In particular, lower expenditure on hardware is to be achieved.

DISCLOSURE OF THE INVENTION

Said object is achieved by a cleaning device and by a method for cleaning items to be cleaned with the features of the independent claims. Advantageous further developments which can be realized individually or in arbitrary combination are shown in the dependent claims.

The terms "have", "comprise", "include" or "incorporate" or arbitrary grammatical deviations therefrom are used in a non-exclusive manner. Accordingly, said terms can relate both to situations in which, along with features introduced by said terms, no further features are present or to situations in which one or several further features are present. For example, the expression "A has B", "A comprises B", "A includes B" or "A incorporates B" can refer both to situations in which, apart from B, there are no further elements in A (i.e. to a situation in which A consists exclusively of B), and to situations in which, in addition to B, one or several further elements are present in A, for example element C, elements C and D or even further elements.

The cleaning device described can be set up, in particular, to carry out a method according to the invention. In reverse, the method can be carried out using the cleaning device according to the invention. Accordingly, the description of optional details of the method can be referred to for the description of optional details of the cleaning device and vice versa.

A cleaning device for cleaning items to be cleaned is proposed in a first aspect. A cleaning device is to be understood as a device which is set up in order to eliminate contaminants which adhere to the items to be cleaned and/or are contained therein, at least in an extensive manner. As an option, the cleaning device can additionally also develop a germ-eliminating action, for example a disinfecting action.

The cleaning device can be selected in particular from the group consisting of a dishwasher and a cleaning and disinfecting device for cleaning containers for accommodating human waste, in particular a bedpan washer disinfector. Such a cleaning device for cleaning containers for accommodating human waste can be designated as cleaning and disinfecting equipment. The cleaning device can be developed, for example, according to the above-described prior art, with the additional features according to the invention described below. A different development is, however, also possible.

Items to be cleaned, in this case, can be understood in general within the framework of the present invention as one or several objects which are to be cleaned. In particular, the items to be cleaned can include one or several containers and in addition, in particular, one or several containers for accommodating human waste. In particular, the cleaning device can be developed for cleaning containers for accommodating human waste. For example, the container can be set up to accommodate waste in quantities of at least 100 ml, in particular in quantities of at least 200 ml or even at least 500 ml or more. The item to be cleaned can be selected from the group consisting of: urine bottles, bed pans, kidney dishes, wash bowls or similar containers which are used, for example, in hospitals and geriatric care facilities.

The container can comprise at least one container edge which can be developed in a rigid or also deformable, in particular flexible manner. Thus, the container can comprise, for example, a vessel with a rigid container wall, for example produced from one or several of the materials glass, plastics, ceramic and metal. As an alternative to this or in addition to it, the container can also comprise a deformable container wall, for example at least one foil bag produced from a plastics material. Thus, the container for human waste can also be developed, for example, entirely or in part as an initially closed receptacle in the shape of a foil bag.

The container can comprise at least one receiving region for human waste, for example at least one cavity. In addition, the container can comprise at least one opening which can be present first of all and/or can also be created at a later time, for example during and/or prior to the cleaning process. The opening can be created, for example, by opening the container mechanically and/or by cutting open and/or tearing open the container. In addition, the opening can be set up to be reversibly or irreversibly opened and/or closed.

The cleaning device includes at least one nozzle system for acting upon the items to be cleaned with at least one cleaning fluid. A nozzle system is to be understood in general as a device by way of which the at least one cleaning fluid can be applied on the container, preferably directly, for example as a result of spraying, dropping or jetting or a combination of the named impacting methods and/or in another manner. The nozzle system can comprise one or several nozzles, for example a plurality of nozzles, in particular at least two nozzles. The nozzles can comprise in particular in each case at least one opening, for example at least one spray opening or a plurality of spray openings, through which the cleaning fluid can be applied to the container.

A cleaning fluid can be understood as an arbitrary liquid which has a cleaning action on the items to be cleaned. For example, the cleaning fluid can be water or an aqueous cleaning liquid with one or several additives such as, for example, at least one cleaner concentrate and/or at least one chemical additive such as, for example, a disinfection agent and/or a rinsing agent. In general, different types of cleaning fluids can also be used.

The nozzle system comprises at least one high pressure nozzle and at least one low pressure nozzle. A nozzle, in this case, is to be understood in general within the framework of the present invention as a device with at least one opening, also designated as a nozzle opening or spray opening, which is set up to generate one or several jets of cleaning fluid. Thus, the nozzle can be a device, for example, which is set up to convert compression energy into kinetic energy.

Independently of the respective actual pressure, within the framework of the present invention the terms high pressure nozzle and low pressure nozzle are used as designations which simply convey that a pressure, a kinetic energy, a pulse or a speed of at least one jet of the cleaning fluid generated by the high pressure nozzle, at the same output pressure prior to passing the respective nozzle, is greater than a pressure or a kinetic energy or a pulse or a speed of at least one jet of the cleaning fluid generated by the low pressure nozzle. In general, the high pressure nozzle can be set up to impact upon the items to be cleaned with one or several jets of the cleaning fluid which are at a higher pressure, a higher speed, a higher pulse or a higher kinetic energy than corresponding jets by means of which the lower pressure nozzle acts upon the items to be cleaned at identical output pressure prior to passing the respective nozzle.

For example, the low pressure nozzle can be set up to enable passage of a large volume flow of the cleaning fluid, whereas the high pressure nozzle can be set up to enable passage of a smaller volume flow. For example, at the identical output pressure prior to passing the respective nozzle, a volume flow or entire volume flow of the cleaning fluid which passes the low pressure nozzle can be greater by at least a factor of 1.5, preferably by at least a factor of 2, in particular by at least a factor of 3, at least a factor of 4 or even at least a factor 5, than a volume flow or entire volume flow of the cleaning fluid which passes the high pressure nozzle.

For example, the high pressure nozzle can comprise a higher flow resistance, in particular a higher overall flow resistance than the low pressure nozzle. Flow resistance can be defined, for example, as the ratio between a pressure difference upstream and downstream of the respective nozzle and an entire volume flow through the nozzle. For example, the high pressure nozzle can comprise a flow resistance which is greater by at least a factor of 1.5 than the flow resistance of the low pressure nozzle, greater preferably by at least a factor of 2 or even by at least a factor of 3, at least a factor of 4 or at least a factor of 5.

As an alternative to this or in addition to it, the high pressure nozzle can comprise a spray opening which is smaller in comparison to the low pressure nozzle. If several spray openings are provided, a total cross section of the spray openings of the high pressure nozzle can, for example, be smaller than a total cross section of the spray openings of the low pressure nozzle. The high pressure nozzle can comprise, for example, at least one nozzle cross section which is smaller than the low pressure nozzle by a factor of 1.5, in a particularly preferred manner a nozzle cross section which is smaller by a factor of 2, at least one nozzle cross section which is smaller by a factor of 5.

A nozzle cross section is to be understood as a total cross section of the at least one nozzle opening of the nozzle, for example in a cutting plane perpendicular to a main direction of flow in which the cleaning fluid flows through the nozzle. If several nozzle openings are provided in the respective nozzle, the nozzle cross sections thereof are to be added up in each case.

In addition, the cleaning device includes at least one pump for conveying the cleaning fluid to the nozzle system. A pump is generally to be understood as a device for transporting and/or for conveying a liquid. For example, a work of a drive of the pump can be provided by a motor, for example an electric motor. The cleaning fluid to be conveyed can be supplied to the pump by means of at least one feed line.

The pump can be connected to at least one fluid tank for providing the cleaning fluid. The fluid tank can include at least one liquid reservoir for receiving the cleaning fluid and/or a constituent part thereof, for example the fluid tank can be realized as a water tank. In addition, the fluid tank can include at least one vapor generator. A vapor generator is to be understood as a device for generating vapor. Vapor can be, for example, water vapor, for example water vapor at a temperature of at least 80° C., preferably of at least 90° C. and in a particularly preferred manner water vapor of at least 100° C. Vapor mixtures, however, are also possible in principle, for example vapor mixtures of water vapor with at least one additional gas component, for example a disinfecting gas. The vapor generator can be a component that is incorporated in the fluid tank or it can also be a separator component.

The pump can be realized with multiple stages. Multiple stages is to be understood as the pump having at least two hydraulic elements which, at the identical drive speed, output in each case a hydraulic output with different hydraulic features with reference to pressure and volume flow.

The pump can comprise at least one low pressure stage and at least one high pressure stage which is mounted downstream of the low pressure stage in a direction of flow of the cleaning fluid. The pump can convey the cleaning fluid from the low pressure stage to the nozzle system at a small amount of pressure. In the high pressure stage the pump can generate a higher pressure than in the low pressure stage and, for example, at the same time can also only convey a smaller volume flow of the cleaning fluid, in particular a volume flow which is smaller by at least 50% than in the lower pressure stage. The at least one low pressure stage and the at least one high pressure stage can be arranged in one common pump housing. The pump housing can consist of fixed components which can serve for guiding the fluid to be conveyed and which can be set up to accommodate the rotating components, such as the drive shaft and pump impellers. In addition, structures which influence the fluid flow in the interior, particularly between the different pump stages, can be present in the pump housing.

In addition, the at least one low pressure stage and the at least one high pressure stage can be driven by a common drive shaft. The common drive shaft can preferably be connected to a common drive unit, for example an electric motor, the driving force of which is transmitted by the drive shaft to the pump. An outlet of the low pressure stage can be connected to an inlet of the high pressure stage.

In addition, the high pressure nozzle and the low pressure nozzle are connected fluidically to the pump. For example, the pump can be connected to the at least one high pressure nozzle and to the at least one low pressure nozzle by means of a common feed line. Branches to the at least one high pressure nozzle and to the at least one low pressure nozzle can lead from the common feed line.

In a preferred manner, an outlet of the high pressure stage can be connected fluidically to the nozzle system.

In addition, the outlet of the low pressure stage can be connected fluidically to the nozzle system by means of at least one bypass by bypassing the high pressure stage. The bypass can be understood as a feed line which connects the outlet of the low pressure stage directly to the common feed line to the nozzle system such that the cleaning fluid bypasses the high pressure stage. The bypass can be arranged with the at least one high pressure stage and the at least one low pressure stage in a common pump housing. The outlet of the high pressure stage and the bypass can open out in a common feed line to the high pressure nozzle and to the low pressure nozzle. The pump can have one or several high pressure stages. If the pump has several high pressure stages, the bypass can be set up to bridge a high pressure stage or also to bridge or to bypass several high pressure stages or all the high pressure stages.

In one embodiment, the pump can comprise at least two high pressure stages which can be connected in series. For example, where there are two high pressure stages that are connected in series, the outlet of a first high pressure stage leads directly and exclusively into an inlet of a second high pressure stage. In said embodiment, the bypass can be connected fluidically to the nozzle system by bypassing the at least two high pressure stages. The cleaning device can comprise several high pressure stages. In a preferred manner, an outlet of a preceding high pressure stage can lead directly to an inlet of a connecting high pressure stage. The outlet of the last high pressure stage in the series can be connected to the common feed line to the nozzle system.

At least one switching member, which is set up to throttle, and preferably to block, a flow of the cleaning fluid from the outlet of the low pressure stage through the bypass, can be arranged in the bypass. A switching member can be understood in general as a component by way of which the flow can be controlled by said component, in particular a valve.

The switching member can include a passive switching member. A passive switching member is to be understood as a switching member which cannot be controlled in an active manner by a control means. For example, the passive switching member can be a pressure-controlled switching member, in particular the switching can include a non-return. A non-return valve is to be understood as a component which allows the cleaning fluid to flow only in one direction and blocks it in another direction.

The switching member can be set up in such a manner that the cleaning fluid is able to flow through the bypass exclusively in the direction of the nozzle system. In a preferred manner, the non-return valve can be developed as a passive non-return ball valve. A non-return ball valve is to be understood in general as a component which has a blocking element which is at least in part ball-shaped. For example, the non-return valve, in particular the non-return ball valve, can comprise at least one blocking element which is preferably developed at least in sections in a ball-shaped manner, the blocking element being pressed into a seat by at least one spring element and as a result closing an opening, it being possible as a result of a sufficient counter pressure of the cleaning fluid to raise the blocking element out of its seat again and to release the opening. A different development of the switching member is basically also possible. Other designs are also conceivable as an alternative to or in addition to a complete or partial development of the non-return valve as a non-return ball valve, in particular as a passive non-return ball valve. Thus, the non-return valve, as an alternative to or in addition to a non-return ball valve, can also include at least one cone valve and/or at least one flap valve. Other designs are also conceivable.

At least one fluidic switching element for adjusting an inflow of the cleaning fluid to the low pressure nozzle is connected upstream of the low pressure nozzle. The fluidic switching element can be arranged in at least one branch which leads to the low pressure nozzle. A fluidic switching element is to be understood as a switching member which is set up to block the low pressure nozzle in a hydraulic manner, for example the fluidic switching element can include at least one blocking valve. The fluidic switching element can be selected, in particular, from the group consisting of: a valve, a tap and a slider. The actuation of the fluidic switching element can be effected in different ways. For example, at least one drive can be provided, selected from a group consisting of: an electric drive, a hydraulic drive, a pneumatic drive, a mechanical drive and an electromagnetic drive. In a particularly preferred manner, an electromagnetic drive can be provided. Other drives, however, are also conceivable.

The above-described switching member which is set up to throttle, in particular to prevent entirely, a flow of the cleaning fluid from the outlet of the low pressure stage through the bypass, can be set up further in such a manner that when the fluidic switching element is open, a flow through the bypass upstream of the low pressure nozzle is made possible and that when the fluidic switching element is closed a flow through the bypass is prevented. Said embodiment is particularly advantageous as it is possible in this way to actuate the low pressure and high pressure stages of the pump in a simple manner.

The cleaning device can comprise at least one control means which is set up to carry out at least one cleaning program. The control means can be central or decentral. For example, the control means can include at least one data processing device, for example at least one processor, in particular a microcontroller. In addition, the control means can comprise one or several interfaces, for example at least one user interface and/or at least one electronic interface. For example, the interface can include a keyboard and/or an operator display by means of which a user can adjust one or several parameters such as, for example, a predefined sequence of one low pressure operation program step and of one high pressure operation program step. An electronic interface can provide, for example, a connection to another machine, for example to a computer or computer network, it being possible to exchange data and/or instructions between the machine and the cleaning device or vice versa. For example, data concerning an anticipated contamination can be communicated to the cleaning device in this manner. The interface can be unidirectional or bidirectional.

The cleaning program can include at least one low pressure mode program step and at least one high pressure mode program step. In the at least one low pressure mode program step of the cleaning program the fluidic switching element can be open and the items to be cleaned be acted upon with the cleaning fluid by means of the at least one low pressure nozzle.

In the at least one high pressure mode program step of the cleaning program the fluidic switching element can be closed and the items to be cleaned can be acted upon with the cleaning fluid exclusively by means of the at least one high pressure nozzle. The control means can be set up in order to carry out the high pressure mode program step at least once after the low pressure mode program step. A different sequence of the low pressure mode and high pressure mode program steps is basically also possible. It is also possible to carry out the low pressure mode program step and/or the high pressure mode program step multiple times.

In addition, the cleaning device can be set up to act upon the items to be cleaned with vapor in at least one program step. The impacting with vapor can be carried out following the low pressure mode and the high pressure mode program steps. A different sequence of cleaning program steps, however, is basically also possible.

In addition, the cleaning device comprises at least one cleaning chamber for receiving the items to be cleaned. A cleaning chamber in terms of the present invention can be a completely or partially closed chamber for accommodating the items to be cleaned. The cleaning chamber can be surrounded in particular completely or in part by at least one housing, for example a housing which is produced entirely or in part from a metal material, for example one or several sheets of high-grade steel. In particular the cleaning chamber can be a closed chamber which is completely surrounded by a housing. The cleaning chamber can comprise in particular at least one opening through which the container to be cleaned can be moved into the interior of the cleaning chamber. The opening can be developed in particular so as to be closable. For example, the cleaning chamber can comprise at least one door for opening and closing the cleaning chamber and for loading the cleaning chamber with items to be cleaned and unloading said items from said chamber. A door is basically to be understood as an arbitrary closure device of the cleaning chamber. The door can be selected, in particular, from the group consisting of: a flap door located on a front side of the cleaning device, in particular a downwardly pivoting flap door; a flap arranged on a top side of the cleaning device; a sliding door; a hood, in particular a hood that can be moved upward.

The cleaning device can comprise at least one holder for receiving the items to be cleaned. A holder is to be understood in general as a device which is set up to receive the container and to fix it relative to the holder. For example, said holder can include at least one rail into which the container can be pushed. As an alternative to this or in addition to it, the holder can include one or several cavities into which the container can be pushed and/or introduced. In this case, the cleaning device can comprise a fixed holder, or also an exchangeable holder, for example by a type of a holder being able to be adapted to the model of container.

The cleaning device can comprise at least one outflow. The outflow can comprise a cross section, for example a diameter or also equivalent diameter of an inlet into the outflow, of at least 30 mm, preferably at least 50 mm and in a particularly preferred manner at least 70 mm or even at least 100 mm. The holder can be set up to empty the items to be cleaned directly or indirectly into the outflow. For example, the holder can be set up to pivot the items to be cleaned in such a manner that they are emptied into an outflow. The emptying can be effected for example in an automatic manner, for example prior to and/or during a cleaning program. For example, the emptying of the items to be cleaned can be effected as the door is closed, in particular if the holder is connected to the door.

In the floor region, the cleaning chamber of the cleaning device can run at least in part in a funnel shaped manner and/or at an angle toward the outflow.

In particular, the outflow can comprise at least one odor trap. An odor trap is to be understood as a device by way of which gases from at least one outflow pipe connected to the outflow can be kept away from the interior of the cleaning chamber. For example, the odor trap can comprise at least one syphon bend. The syphon bend can comprise, for example, a quantity of liquid as an odor trap. In addition, the cleaning device can preferably comprise at least one bypass to conduct gas and vapor out of the cleaning chamber by bypassing the odor trap, for example by bypassing the syphon bend, into the outflow, preferably under pressure. To this end, the bypass can comprise, for example, one or several pipe lines which connect the cleaning chamber to the outflow by bypassing the odor trap, as well as, as an option, at least one non-return valve and/or at least one other type of valve which prevents gases from the outflow and/or from an outflow pipe connected to the outflow penetrating completely or in part through the bypass into the cleaning chamber.

In a further aspect, a method for cleaning items to be cleaned is proposed. In the method the items to be cleaned are acted upon with at least one cleaning fluid by means of at least one nozzle system and a pump is used to convey the cleaning fluid to the nozzle system, in particular the multi-stage pump described in a first aspect of the invention. The nozzle system comprises at least one high pressure nozzle and at least one low pressure nozzle. Reference can be made to the above description as regards possible developments and definitions of the high pressure nozzle and the low pressure nozzle. In addition, the high pressure nozzle and the low pressure nozzle are connected fluidically to the pump. An inflow of the cleaning fluid to the low pressure nozzle is adjusted by means of at least one of the fluid switching elements connected upstream of the low pressure nozzle.

The method can include the carrying out of at least one cleaning program. In at least one low pressure mode program step of the cleaning program the fluidic switching element can be open and the items to be cleaned can be acted upon with the cleaning fluid by means of the at least one low pressure nozzle. In at least one high pressure mode program step of the cleaning program the fluidic switching element can be closed and the items to be cleaned can be acted upon with the cleaning fluid by means of the at least one high pressure nozzle, preferably exclusively by means of the at least one high pressure nozzle.

The pump can comprise at least one low pressure stage and at least one high pressure stage which is connected downstream of the low pressure stage. In the low pressure mode program step cleaning fluid can be directed from the low pressure stage past the high pressure stage by means of at least one bypass and can be supplied to the nozzle system, for example in a direct manner. In the high pressure mode program step, on account of the closing of the fluidic switching element, a pressure of the cleaning fluid at the nozzle system can be increased compared to the low pressure mode program step, as a result of which the at least one switching member in the bypass can be closed and cleaning fluid can be conducted out of the low pressure stage through the high pressure stage to the nozzle system.

In particular, the cleaning device proposed in the first aspect of the invention can be used in the proposed method, for example according to one of the above-described embodiments and/or to one of the embodiments described in more detail below.

For example, a cleaning program can start with a cleaning process in low pressure mode or can include at least one cleaning process in low pressure mode at least at the beginning of the cleaning program. The fluidic switching element can be open for this purpose. The control means can start up the pump, run it in the low pressure stage and convey the cleaning fluid via the common feed line to the at least one low pressure nozzle and the at least one high pressure nozzle. By using both nozzles a high volume flow can be set at the same time as low pressure. In said program step, in particular coarse contaminants or also possibly cellulose located in the items to be cleaned can be flushed out. The high volume flow is additionally advantageous as the odor trap connected to the cleaning chamber is able to be flushed through well. A volume flow of at least 1 l/s can usually be necessary to flush through the odor trap.

Cleaning in high pressure mode can be effected in a following cleaning step. The fluidic switching element is closed for this purpose. High pressure can be set by just using the high pressure nozzles. The non-return valve at the outlet of the low pressure stage can block off the bypass. The pump can then work in high pressure mode such that the cleaning fluid, for example, is conducted from the low pressure stage into the high pressure stage, in which the pressure can be increased further. The cleaning fluid can be conveyed at high pressure by means of the common feed line to the at least one high pressure nozzle. The cleaning fluid emerging out of the at least one high pressure nozzle can, for example with reference to the volume flow, have a high energy content, for example a high kinetic energy and/or a high pulse. In said program step, a seriously improved cleaning action can be achieved, for example in a boundary layer between dirt and items to be cleaned, in relation to the preceding program step, preferably at the same time at a reduced volume flow.

The further cleaning program can comprise further sequences of low pressure mode program steps and high pressure mode program steps. Disinfection steps and/or drying steps can also be effected as an option.

The proposed cleaning device comprises numerous differences and advantages in particular also in relation to the above-mentioned prior art. Thus, in DE 198 12 231 A1 different pressures are achieved at different speeds of a pump. A corresponding control means is required for this. DE 195 21 21 536 C2 describes a high pressure cleaner with two pumps. In this case, however, the second pump is developed as a dosing pump for a cleaning agent. Nevertheless, said equipment is set up for cleaning with two pressures in the cleaning fluid. The first lower pressure, however, in this case, is not generated in the equipment by a pump, but only by the pressure in a supply line on site. Accordingly, on-site measures which can be avoided according to the invention are necessary for the operation of the equipment. DE 1 503 853 does not describe a two-stage centrifugal pump, but rather a centrifugal pump combined with a separate piston pump which feeds a separate nozzle. The separate piston pump also has an own separate drive.

In summary, within the framework of the present invention the following embodiments are particularly preferred:
Embodiment 1: cleaning device for cleaning items to be cleaned, including at least one nozzle system for acting upon the items to be cleaned with at least one cleaning fluid, additionally including at least one pump for conveying the cleaning fluid to the nozzle system, the nozzle system comprising at least one high pressure nozzle and at least one low pressure nozzle, the high pressure nozzle and the low pressure nozzle being connected fluidically to the pump, at least one fluidic switching element for adjusting an inflow of the cleaning fluid to the low pressure nozzle being connected upstream of the low pressure nozzle.

Embodiment 2: cleaning device according to the preceding embodiment, the pump being connected to the at least one high pressure nozzle and to the at least one low pressure nozzle by means of a common feed line.

Embodiment 3: cleaning device according to the preceding embodiment, branches to the at least one high pressure nozzle and to the at least one low pressure nozzle leading from the common feed line.

Embodiment 4: cleaning device according to the preceding embodiment, the fluidic switching element being arranged in at least one branch which leads to the low pressure nozzle.

Embodiment 5: cleaning device according to one of the preceding embodiments, the fluidic switching element including at least one blocking valve.

Embodiment 6: cleaning device according to one of the preceding embodiments, the fluidic switching element being selected from the group consisting of a valve, a tap and a slider.

Embodiment 7: cleaning device according to one of the preceding embodiments, the pump being developed with multiple stages.

Embodiment 8: cleaning device according to the preceding embodiment, the pump comprising at least one low pressure stage and at least one high pressure stage which is connected downstream of the low pressure stage in the direction of flow of the cleaning fluid.

Embodiment 9: cleaning device according to the preceding embodiment, the at least one low pressure stage and the at least one high pressure stage being arranged in a common pump housing.

Embodiment 10: cleaning device according to either of the two preceding embodiments, the at least one low pressure stage and the at least one high pressure stage being driven by a common drive shaft.

Embodiment 11: cleaning device according to one of the three preceding embodiments, an outlet of the low pressure stage being connected to an inlet of the high pressure stage, an outlet of the high pressure stage being connected fluidically to the nozzle system.

Embodiment 12: cleaning device according to the preceding embodiment, the outlet of the low pressure stage being additionally connected fluidically to the nozzle system by means of at least one bypass by bypassing the high pressure stage.

Embodiment 13: cleaning device according to the preceding embodiment, the outlet of the high pressure stage and the bypass opening out in a common feed line to the high pressure nozzle and the low pressure nozzle.

Embodiment 14: cleaning device according to either of the two preceding embodiments, the pump comprising at least two high pressure stages, the bypass being connected fluidically to the nozzle system by bypassing the at least two high pressure stages.

Embodiment 15: cleaning device according to the preceding embodiment, the at least two high pressure steps being connected in series.

Embodiment 16: cleaning device according to one of the four preceding embodiments, the bypass being arranged in a common pump housing with the at least one high pressure stage and the at least one low pressure stage.

Embodiment 17: cleaning device according to one of the five preceding embodiments, at least one switching member being arranged in the bypass.

Embodiment 18: cleaning device according to the preceding embodiment, the switching member being set up to throttle, preferably to block, a flow of the cleaning fluid from the outlet of the low pressure stage through the bypass.

Embodiment 19: cleaning device according to either of the two preceding embodiments, the switching member including a passive switching member.

Embodiment 20: cleaning device according to the preceding embodiment, the passive switching member being a pressure-controlled switching member.

Embodiment 21: cleaning device according to one of the four preceding embodiments, the switching member including a non-return valve.

Embodiment 22: cleaning device according to the preceding embodiment, the non-return valve being a non-return ball valve.

Embodiment 23: cleaning device according to one of the six preceding embodiments, the switching member being set up in such a manner that it is possible for the cleaning fluid to flow through the bypass exclusively in the direction of the nozzle system.

Embodiment 24: cleaning device according to one of the seven preceding embodiments, the switching member being set up in such a manner that when the fluidic switching element is open, flow through the bypass is made possible and that when the fluid switching element is closed flow through the bypass is prevented.

Embodiment 25: cleaning device according to one of the preceding embodiments, the cleaning device comprising at least one control means, the control means being set up to carry out at least one cleaning program, in at least one low pressure mode program step of the cleaning program, the fluidic switching element being open and the items to be cleaned being able to be acted upon with the cleaning fluid by means of the at least one low pressure nozzle, in at least one high pressure mode program step of the cleaning program the fluidic switching element being closed and the items to be cleaned being able to be acted upon with the cleaning fluid exclusively by means of the at least one high pressure nozzle.

Embodiment 26: cleaning device according to the preceding embodiment, the control means being set up to carry out the high pressure mode program step at least once after the low pressure mode program step.

Embodiment 27: cleaning device according to either of the two preceding embodiments, the control means including at least one data processing device.

Embodiment 28: cleaning device according to one of the preceding embodiments, the cleaning device comprising at least one cleaning chamber for accommodating the items to be cleaned.

Embodiment 29: cleaning device according to one of the preceding embodiments, the cleaning device being selected from the group consisting of a dishwasher and a cleaning and disinfecting apparatus for cleaning containers for receiving human waste, in particular a bedpan.

Embodiment 30: cleaning device according to one of the preceding embodiments, the cleaning device being developed for cleaning containers for receiving human waste.

Embodiment 31: cleaning device according to one of the preceding embodiments, the cleaning device comprising at least one outflow, the cleaning device being set up to dispose of waste contained in the items for cleaning into the outflow.

Embodiment 32: cleaning device according to the preceding embodiment, the outflow comprising at least one odor trap.

Embodiment 33: cleaning device according to either of the two preceding embodiments, the outflow comprising a cross section of at least 30 mm, preferably at least 50 mm and in a particularly preferred manner at least 70 mm or even at least 100 mm.

Embodiment 34: cleaning device according to one of the three preceding embodiments, the cleaning device comprising at least one holder for accommodating the items to be cleaned, the holder being set up to pivot the items to be cleaned in such manner that they are emptied into the outflow.

Embodiment 35: cleaning device according to one of the preceding embodiments, it being possible to act upon the pump with the cleaning fluid via at least one feed line.

Embodiment 36: cleaning device according to one of the preceding embodiments, the pump being connected to the at least one fluid tank for providing the cleaning fluid.

Embodiment 37: cleaning device according to the preceding embodiment, the fluid tank including at least one liquid reservoir.

Embodiment 38: cleaning device according to either of the two preceding embodiments, the fluid tank additionally including at least one vapor generator.

Embodiment 39: cleaning device according to the preceding embodiment, the cleaning device being set up to act upon the items to be cleaned with vapor in at least one program step.

Embodiment 40: method for cleaning items to be cleaned, the items to be cleaned being acted upon with at least one cleaning fluid by means of the at least one nozzle system, a pump being used for conveying the cleaning fluid to the nozzle system, the nozzle system comprising at least one high pressure nozzle and at least one low pressure nozzle, the high pressure nozzle and the low pressure nozzle being connected fluidically to the pump, an inflow of the cleaning fluid to the low pressure nozzle is adjusted by means of at least one fluidic switching element connected upstream of the low pressure nozzle.

Embodiment 41: method according to the preceding embodiment, the method including the carrying out of at least one cleaning program, in at least one low pressure mode program step of the cleaning program the fluidic switching element being open and the items to be cleaned being acted upon with the cleaning fluid by means of the at least one low pressure nozzle, in at least one high pressure mode program step of the cleaning program the fluidic switching element being closed and the items to be cleaned being acted upon with the cleaning fluid exclusively by means of the at least one high pressure nozzle.

Embodiment 42: method according to the preceding embodiment, the pump comprising at least one low pressure stage and at least one high pressure stage connected downstream of the low pressure stage, in the low pressure mode program step cleaning fluid being conducted out of the low pressure stage past the high pressure stage by means of at least one bypass and supplied to the nozzle system, in the high pressure mode program step, on account of the closing of the fluidic switching element, a pressure of the cleaning fluid at the nozzle system being increased in relation to the low pressure mode program step, as a result of which at least one switching member is closed in the bypass and cleaning fluid is conducted out of the low pressure stage through the high pressure stage to the nozzle system.

Embodiment 43: method according to one of the three preceding embodiments, a cleaning device according to one of the preceding claims which relate to a cleaning device being used in the method.

BRIEF DESCRIPTION OF THE FIGURES

Further details and features of the invention are produced from the following description of preferred exemplary embodiments, in particular in conjunction with the subclaims. In this connection, the respective features can be realized individually on their own or as a plurality in combination with one another. The invention is not limited to the exemplary embodiments. The exemplary embodiments are shown schematically in the figures. Identical reference numerals in the individual figures in this case designate identical or functionally identical elements or elements which correspond to one another regarding their functions.

In detail.

DESCRIPTION OF THE EXEMPLARY EMBODIMENTS

Figure 1:
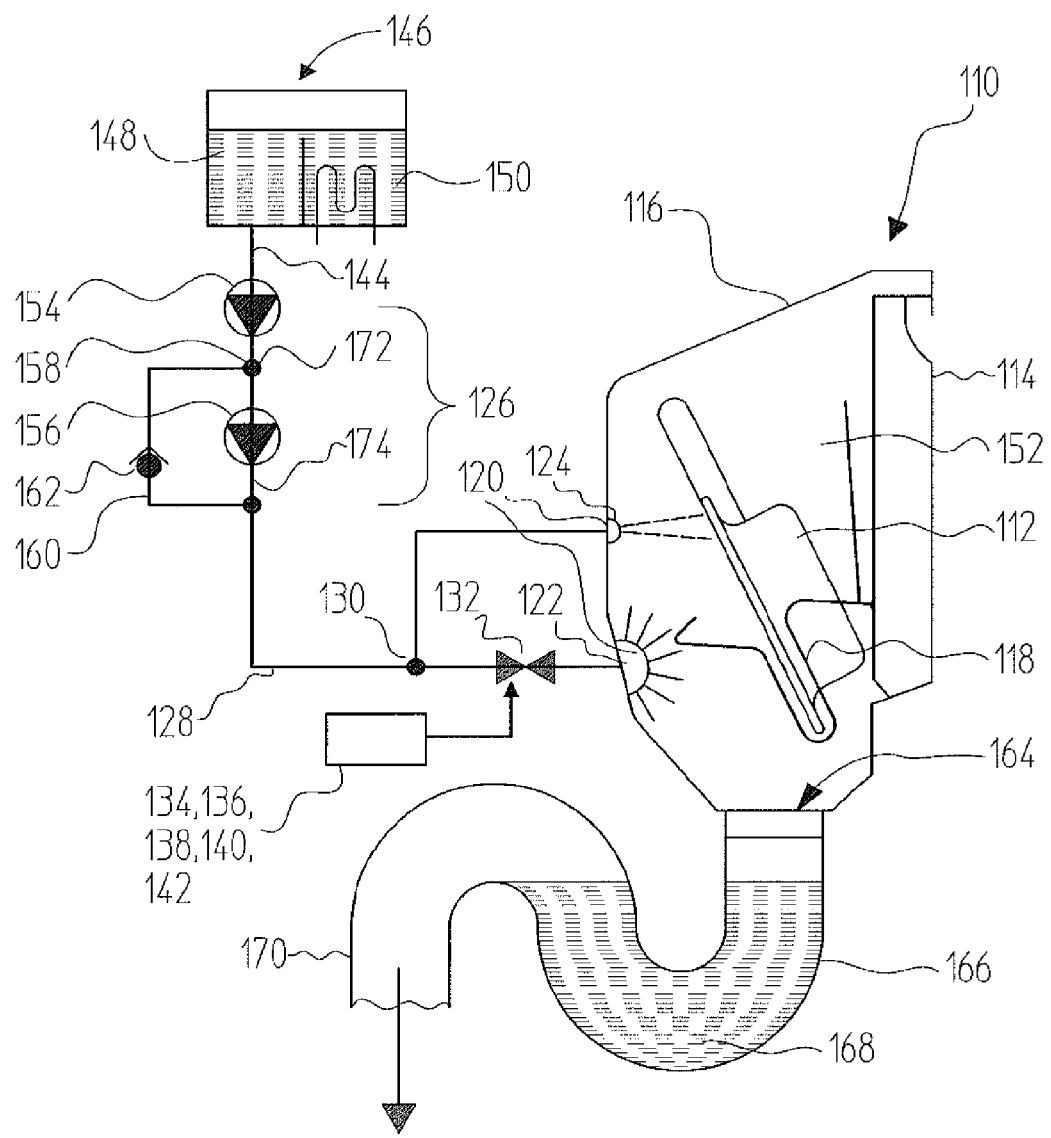
FIG. 1 shows a cleaning device according to the invention with a low pressure nozzle and a high pressure nozzle.

An exemplary embodiment of a cleaning device 110 according to the invention for cleaning items to be cleaned 112 is shown in FIG. 1. The cleaning device 110 can be developed, for example, as a cleaning device for cleaning containers for receiving human waste, in particular a cleaning and disinfecting apparatus and/or a flusher-disinfector. The items to be cleaned 112 can be, for example, a container for receiving human waste. The items to be cleaned can be introduced into a cleaning chamber 116 through a door 114, for example a front flap as shown in FIG. 1, or a door which is developed in another manner. The opening and closing of the door 114 can be effected automatically and/or manually. The items to be cleaned 112 can be fixed in the cleaning chamber 116 by a holder 118, for example a wire frame or another type of holder 118.

The cleaning chamber 116 comprises a nozzle system 120 in order to act upon the items to be cleaned 112 with a cleaning fluid. The cleaning fluid can be, for example, water and/or a cleaning liquid with an additive of cleaner concentrate and/or a chemical additive. The nozzle system 120 includes at least one low pressure nozzle 122 and at least one high pressure nozzle 124. The high pressure nozzle 124 comprises, for example, a smaller nozzle cross section and/or a higher flow resistance than the low pressure nozzle 122. For example, the high pressure nozzle 124 can comprise a smaller spray opening than the low pressure nozzle 122.

The cleaning device 110 comprises at least one pump 126 which is connected fluidically to the low pressure nozzle 122 and to the high pressure nozzle 124. For example, the pump 126 can be connected to the low pressure nozzle 122 and to the high pressure nozzle 124 by means of a common feed line 128. The common feed line 128 can comprise branches 130 to the low pressure nozzle 122 and to the high pressure nozzle 124. The branch which leads to the low pressure nozzle 122 comprises at least one fluidic switching element 132, for example a blocking valve and/or a tap and/or a slider. The inflow of the cleaning fluid to the low pressure nozzle 122 is adjusted by way of the fluidic switching element 132.

The cleaning device 110 comprises a control means 134 which is set up to open and close the fluidic switching element 132. The control means 134 is only shown schematically in FIG. 1. The control means 134 can comprise, for example, at least one data processing means 136 and, as an option, at least one data storage means 138. In addition, the control means 134 can comprise, for example, one or several interfaces 140, for example one or several control elements 142, for example selected from the group consisting of: switches keyboards, operating displays and displaying devices.

The pump 126 can be connected by means of a feed line 144 to a fluid tank 146 which includes at least one liquid reservoir 148. For example, the pump 126 can be acted upon with cleaning fluid from the liquid reservoir 148. As an option, the fluid tank 146 can comprise a vapor generator 150 to provide vapor for a possible disinfection step during a cleaning program.

In addition, the control means 134 can be set up to carry out at least one cleaning program. The cleaning program can include at least one low pressure mode program step and at least one high pressure mode program step. For example, a high pressure mode program step can be effected after a low pressure mode program step. But another sequence is also possible. For example, several high pressure mode program steps can be carried out one after another.

In the low pressure mode program step, the fluidic switching element 132 can be opened by the control means 134 such that cleaning fluid is able to enter into an interior 152 of the cleaning chamber 116 through the low pressure nozzle 122 and the high pressure nozzle 124. As the high pressure nozzle 124 and the low pressure nozzle 122 are both used, the entry of the cleaning fluid into the cleaning chamber 116 can result in a large volume flow and low pressure. The pump 126 can comprise several pump stages, for example a low pressure stage 154 and a high pressure stage 156. The high pressure stage 156 can be arranged downstream of the low pressure stage 154 in the direction of flow of the cleaning fluid. In addition, by bypassing the high pressure stage 156 by means of a bypass 160, an outlet of the low pressure stage 158 can be connected to the nozzle system 120. The bypass 160 comprises at least one switching member 162 to be able to block the bypass 160 against the cleaning fluid flowing through and only to allow the cleaning fluid to flow through in the direction of the nozzle system 120. When a fluidic switching element 132 is open, flow through the bypass 160 is possible. The bypass 160 can open out in the common feed line 128 to the nozzle system 120.

The cleaning device 110 can comprise an outflow 164 which can be arranged, for example, on the floor of the cleaning chamber 116. The holder 118 can be set up to empty the items to be cleaned 112 into the outflow 164. The outflow 164 can preferably comprise an odor trap 166, for example a syphon bend. The odor trap 166 can comprise, for example, a liquid store 168 as an odor trap. The odor trap 166 can be connected, for example, to at least one outlet pipe 170. The large volume flow of the cleaning fluid in the low pressure mode program step can ensure that the odor trap 166 is flushed through well.

In the high pressure mode program step, the fluidic switching element 132 can be closed by the control means 134 such that the cleaning fluid is only able to enter the interior 152 of the cleaning chamber 116 through the high pressure nozzle 124. As the system pressure is increased, the switching member 162 in the bypass 160 is closed such that no cleaning fluid flows from the outlet of the high pressure stage to the inlet of the high pressure stage. The outlet of the low pressure stage 158 can be connected to an inlet of the high pressure stage 172. An outlet of the high pressure stage 174 can open out in the common feed line 128 to the nozzle system 120. During the high pressure mode program step, the cleaning fluid leaves the high pressure nozzle 124 and enters the interior 152 of the cleaning chamber 116 with a small volume flow and at high pressure. As a result, an improved cleaning performance can be achieved compared to a cleaning performance in the low pressure mode program step.

Figure 2:
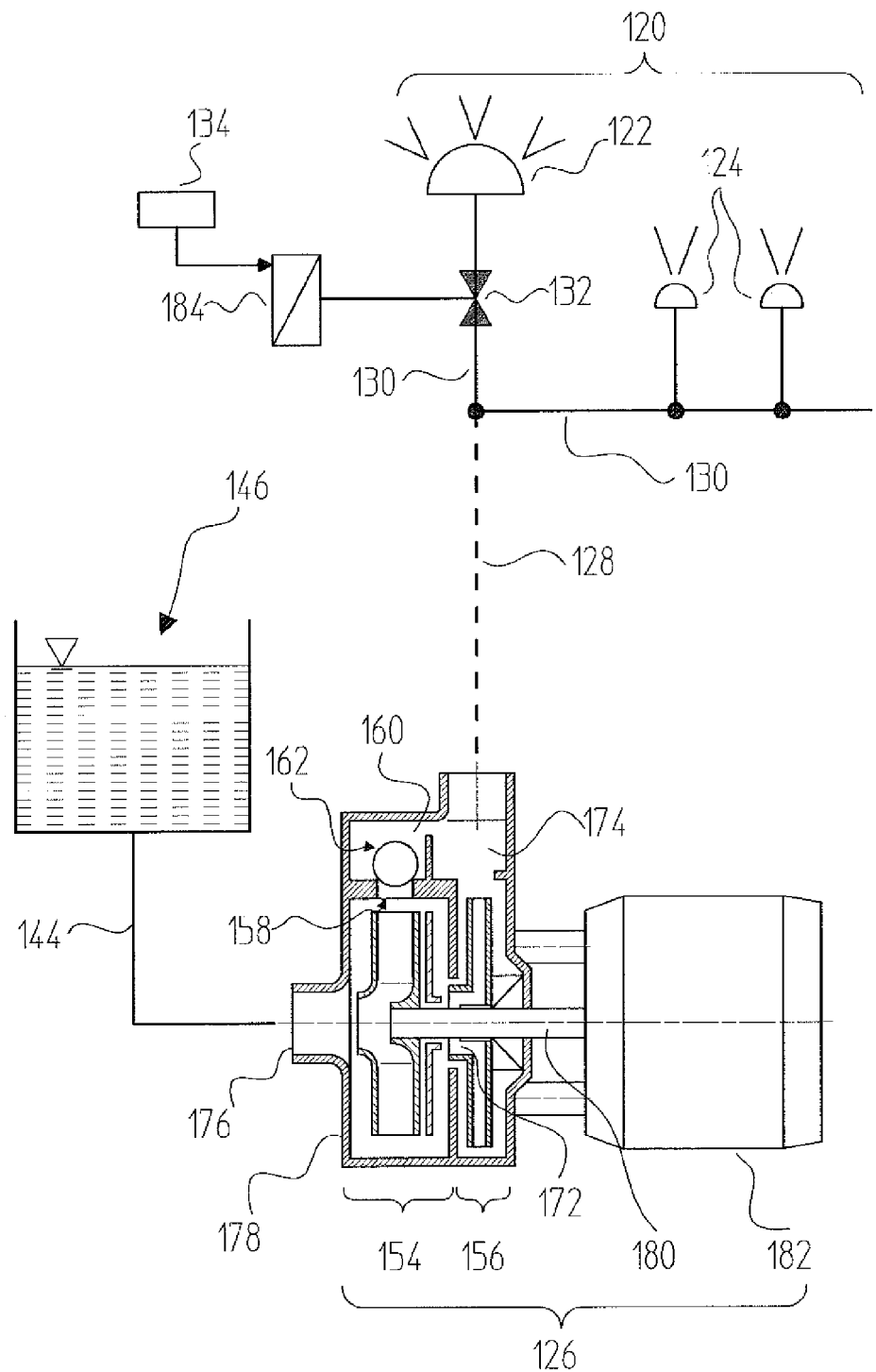
FIG. 2 shows a pump according to the invention and a nozzle system according to the invention.

FIG. 2 shows an exemplary embodiment of a pump 126 according to the invention. An inlet 176 of the pump 126 can be connected to the fluid tank 146 by means of the feed line 144. The low pressure stage 154 and the high pressure stage 156 can be arranged in a common pump housing 178. The low pressure stage 154 can comprise a large volume and large flow areas in the pump 126, whereas the high pressure stage 156 can comprise a relatively smaller volume and relatively smaller flow areas in the pump 126. The low pressure stage 154 and the high pressure stage 156 can be driven by a common drive shaft 180. The drive shaft 180 can be driven by a drive means, for example a motor 182, in particular an electric motor. Such a development of a low pressure system and a high pressure system in one installation unit is particularly preferred as expenditure on construction is reduced, a number of components are reduced and a space requirement is smaller compared to low pressure systems and high pressure systems from the prior art.

The cleaning fluid can be conveyed from the fluid tank 146 to the inlet of the pump 176 by means of the feed line 144. For a low pressure mode program step, the control means 134 transmits, for example, a program parameter, for example a program parameter which characterizes the low pressure mode program step, to a control element 184 of the fluidic switching element 132. The control element 184 opens the fluidic switching element 132. The cleaning fluid can pass from the inlet of the pump 176 into the low pressure stage 154. The bypass 160 with the switching member 162 can branch off at the outlet of the low pressure stage 154. The switching member 162 of the bypass 160 can block the direct outlet of the low pressure stage toward the nozzle system 120. The switching member 162 can be developed, for example, as a passive switching member, preferably as a pressure-controlled switching member, in a particularly preferred manner as a non-return valve, in particular as a non-return ball valve. When the fluidic switching element 132 is open, the cleaning fluid can leave the low pressure stage 154 through the bypass 160 and pass through the common feed line 128 to the low pressure nozzle 122 and the high pressure nozzles 124.

For a high pressure mode program step, the control means 134 transmits a program parameter, for example a program parameter which characterizes the high pressure mode program step, to the control element 184 of the fluidic switching element 132. The control element 184 closes the fluidic switching element 132. Where the fluidic switching element 132 is closed, the pressure in the nozzle system 120 can be increased and the switching member 162 can block the output of the low pressure stage 158. The cleaning fluid cannot leave the pump 126 via the bypass 160, but passes by means of the inlet of the high pressure stage 172, which is connected to the outlet of the low pressure stage 154, into the high pressure stage 156. The cleaning fluid can pass from the outlet of the high pressure stage 174 to the high pressure nozzles 124 by means of the common feed line 128. Said implementation is particularly preferred as the low pressure system and the high pressure system are able to be controlled in a simple manner.

Further embodiments, for example embodiments in which the pump 126 comprises more than one high pressure stage 156, are possible. The at least two high pressure stages 156 can be arranged, for example, in series. Said arrangement in series can lead to a further increase in pressure. The outlet of a preceding high pressure stage can lead directly into an inlet of the following high pressure stage. The outlet of the last high pressure stage 174 of the series can be connected to the common feed line 128. The bypass 160 can bypass all the high pressure stages 156 in the embodiment in which the pump 126 comprises more than one high pressure stage 156.

LIST OF REFERENCES

110 Cleaning device
112 Items to be cleaned
114 Door
116 Cleaning chamber
118 Holder
120 Nozzle system
122 Low pressure nozzle
124 High pressure nozzle
126 Pump
128 Common feed line
130 Branches
132 Fluidic switching element
134 Control means
136 Data processing means
138 Data storage means
140 Interfaces
142 Control elements
144 Feed line
146 Fluid tank
148 Liquid reservoir
150 Vapor generator
152 Interior
154 Low pressure stage
156 High pressure stage
158 Outlet of the low pressure stage
160 Bypass
162 Switching member
164 Outflow
166 Odor trap
168 Liquid store
170 Outflow pipe
172 Inlet of the high pressure stage
174 Outlet of the high pressure stage
176 Inlet of the pump
178 Pump housing
180 Common drive shaft
182 Motor
184 Control element

The invention claimed is:

1. A cleaning device for cleaning items to be cleaned, including at least one nozzle system for acting on the items to be cleaned with at least one cleaning fluid, additionally including at least one pump for conveying the cleaning fluid to the nozzle system; wherein:
the nozzle system comprises at least one high pressure nozzle and at least one low pressure nozzle,
the high pressure nozzle and the low pressure nozzle are connected fluidically to the pump,
at least one fluidic switching element for adjusting an inflow of the cleaning fluid to the low pressure nozzle is connected upstream of the low pressure nozzle,
the cleaning device includes at least one of: a dishwasher, and cleaning and disinfecting equipment, and
the pump comprises multiple stages including at least one low pressure stage and at least one high pressure stage which is mounted downstream of the low pressure stage in a direction of flow of the cleaning fluid, an outlet of the low pressure stage is connected to an inlet of the high pressure stage, an outlet of the high pressure stage is connected fluidically to the nozzle system, and the outlet of the low pressure stage is connected fluidically to the nozzle system by means of a bypass bypassing the high pressure stage.

2. The cleaning device as claimed in claim 1, wherein the pump is connected to the at least one high pressure nozzle and the at least one low pressure nozzle via a common supply line.

3. The cleaning device as claimed in claim 2, wherein branches lead to the at least one high pressure nozzle and to the at least one low pressure nozzle from the common supply line.

4. The cleaning device as claimed in claim 3, wherein the fluidic switching element is arranged in at least one branch which leads to the low pressure nozzle.

5. The cleaning device as claimed in claim 1, wherein the at least one low pressure stage and the at least one high pressure stare are driven by a common drive shaft.

6. The cleaning device as claimed in claim 1, wherein the outlet of the high pressure stage and the bypass open out in a common feed line to the high pressure nozzle and to the low pressure nozzle.

7. The cleaning device as claimed in claim 1, wherein the bypass is arranged with the at least one high pressure stage and the at least one low pressure stage in a common pump housing.

8. The cleaning device as claimed in claim 1, wherein at least one switching member is arranged in the bypass.

9. The cleaning device as claimed in claim 8, wherein the switching member is set up in such a manner that when the fluidic switching element is open, flow through the bypass is made possible and when the fluidic switching element is closed flow through the bypass is prevented.

10. The cleaning device as claimed in claim 1, wherein the cleaning device comprises at least one control means, wherein the control means is set up in order to carry out at least one cleaning program, wherein in at least one low pressure mode program step of the cleaning program the fluidic switching element is open and the items to be cleaned can be acted upon with the cleaning fluid by means of the at least one low pressure nozzle, wherein in at least one high pressure mode program step of the cleaning program the fluidic switching element is closed and the items to be cleaned can be acted upon with the cleaning fluid exclusively by means of the at least one high pressure nozzle.

11. A method for cleaning items to be cleaned, wherein the items to be cleaned are acted upon with at least one cleaning fluid by means of at least one nozzle system, wherein a pump is used to convey the cleaning fluid to the nozzle system, wherein the nozzle system comprises at least one high pressure nozzle and at least one low pressure nozzle, wherein the high pressure nozzle and the low pressure nozzle are fluidically connected to the pump, wherein an inflow of the cleaning fluid to the low pressure nozzle is adjusted by means of at least one fluidic switching element which is connected upstream of the low pressure nozzle; wherein:

the pump comprises multiple stages including at least at least one low pressure stage and at least one high pressure stage which is mounted downstream of the low pressure stage in a direction of flow of the cleaning fluid, and an outlet of the low pressure stage is connected to an inlet of the high pressure stage, an outlet of the high pressure stage is connected fluidically to the nozzle system, and the outlet of the low pressure stage is connected fluidically to the nozzle system by means of at least one bypass bypassing the high pressure stage.

12. The method as claimed in claim 11, wherein the method includes the carrying out of at least one cleaning program, wherein in at least one low pressure mode program step of the cleaning program the fluidic switching element is open and the items to be cleaned are acted upon with the cleaning fluid by means of the at least one low pressure nozzle, wherein in at least one high pressure mode program step of the cleaning program the fluidic switching element is closed and the items to be cleaned are acted upon with the cleaning fluid exclusively by means of the at least one high pressure nozzle.

13. The method as claimed in claim 12, wherein in the low pressure mode program step cleaning fluid is conducted from the low pressure stage past the high pressure stage by means of at least one bypass and is supplied to the nozzle system, wherein in the high pressure mode program step, on account of the closing of the fluidic switching element, a pressure of the cleaning fluid in the nozzle system is increased compared to the low pressure mode program step, as a result of which at least one switching member in the bypass is closed and cleaning fluid is conducted from the low pressure stage through the high pressure stage to the nozzle system.

\* \* \* \* \*